United States Patent
Qiu et al.

(10) Patent No.: US 7,211,149 B2
(45) Date of Patent: May 1, 2007

(54) METHOD FOR APPLYING A COATING TO A MEDICAL DEVICE

(75) Inventors: Yongxing Qiu, Duluth, GA (US); Lynn Cook Winterton, Alpharetta, GA (US); John Martin Lally, Lilburn, GA (US); Yasuo Matsuzawa, Roswell, GA (US); Rafael Victor Andino, Lawrenceville, GA (US); Allen Gilliard, Buford, GA (US)

(73) Assignee: Novartis AG, Basel (CH)

( * ) Notice: Subject to any disclaimer, the term of this patent is extended or adjusted under 35 U.S.C. 154(b) by 199 days.

(21) Appl. No.: 11/029,619

(22) Filed: Jan. 5, 2005

(65) Prior Publication Data

US 2005/0196520 A1    Sep. 8, 2005

Related U.S. Application Data

(62) Division of application No. 10/153,007, filed on May 22, 2002, now Pat. No. 6,858,248.

(60) Provisional application No. 60/301,260, filed on Jun. 27, 2001, provisional application No. 60/294,396, filed on May 30, 2001.

(51) Int. Cl.
  *B05C 19/02* (2006.01)
(52) U.S. Cl. ....................... 118/429; 134/901

(58) Field of Classification Search ................ 118/429, 118/500; 422/292, 297, 300; 134/901, 184–186, 134/56

See application file for complete search history.

(56) References Cited

U.S. PATENT DOCUMENTS

| | | | | |
|---|---|---|---|---|
| 4,575,299 A | * | 3/1986 | Layton et al. | 414/222.05 |
| 4,691,725 A | * | 9/1987 | Parisi | 134/184 |
| 4,710,199 A | * | 12/1987 | Suter | 8/507 |
| 5,339,843 A | * | 8/1994 | Benedict et al. | 134/56 R |
| 5,824,276 A | * | 10/1998 | Janssen et al. | 422/292 |

* cited by examiner

*Primary Examiner*—Brenda A. Lamb
(74) *Attorney, Agent, or Firm*—Jian Zhou

(57) ABSTRACT

This invention provides a method for efficiently applying a coating to each of a plurality of objects selected from the group consisting of ophthalmic lenses, molds for making ophthalmic lenses, and other medical devices, the method comprising dipping the plurality of objects into a coating bath containing a coating solution having a coating material; and creating with a means a convective current flow and thereby forcing a coating solution flowing over and under each of the plurality of ophthalmic lenses. In a preferred embodiment, the plurality of objects are held in baskets which are pre-conditioned to have a first layer of polyelectrolytes and a second layer of aqueous solution or have a mixed layer of polyelectrolytes and aqueous solution on the surfaces of the baskets.

14 Claims, No Drawings

METHOD FOR APPLYING A COATING TO A MEDICAL DEVICE

This application is a division of U.S. patent application Ser. No. 10/153,007, now U.S. Pat. No. 6,858,248, filed May 22, 2002, which claims benefits under 35 U.S.C. §119(e) of U.S. provisional patent application Nos. 60/294,396 filed May 30, 2001 and 60/301,260 filed Jun. 27, 2001.

This invention relates to a method of applying efficiently a uniform coating to an object, especially to an ophthalmic lens or to a mold for making an ophthalmic lens.

BACKGROUND

Many devices used in biomedical applications require that the bulk of the device have one property, while the surface of the device has another property. For example, contact lenses may have high oxygen permeability through the lens to maintain good corneal health. However, materials that exhibit exceptionally high oxygen permeability (e.g. polysiloxanes) are typically hydrophobic and will adhere to the eye. Thus, a contact lens generally has a core or bulk material that is highly oxygen permeable and hydrophobic, and a surface that has been treated or coated to increase hydrophilic properties, thereby allowing the lens to freely move on the eye without adhering excessive amounts of tear lipid and protein.

In order to modify the hydrophilic nature of a relatively hydrophobic contact lens material, a coating may be applied onto the surface of a contact lens using a number of technologies, including a plasma treatment process, a Langmuir-Blodgett deposition process, a controlled spin casting process, a chemisorption process, a vapor deposition and a layer-by-layer polymer adsorption process. The layer-by-layer polymer adsorption (LbL) process could be one useful process for increasing hydrophilic properties of contact lenses. The prior art teaches that an article having hydrophilic surfaces can be coated using a LbL process, where the article having hydrophilic surfaces is dipped in a polyelectrolyte solution (e.g., polycations such as polyallylamine or polyethyleneimine). However, the prior art teaches that, prior to dipping, the surfaces of the article are treated in order to create surfaces having an affinity for the polyelectrolyte.

It was unexpectedly discovered by some of us that a LbL process can be used in coating hydrophobic contact lenses in dry or wet state without any pretreatment (WO9935520). By dipping iteratively lenses in an alternating fashion to a polyanion (e.g., polyacrylic acid, PAA) solution and a polycation (polyallylamine hydrochloride, PAH) solution, a hydrophilic surface can be coated onto the lenses.

During a LbL process, each of a plurality of lenses is generally held in a lens carrying cage which comprises a male and female basket halves. Many of such cages can be affixed together to form trays of baskets. Such trays may then be placed side-by-side to allow hundreds or thousands of lenses being simultaneously processed with a coating solution. However, there are several problems associated with the LbL coating processes, which could affect the quality of coatings on lenses. One problem is the adhesion of lenses to baskets which hold them. Since lens-holding baskets and/or trays generally have hydrophobic surfaces, lenses have a tendency to adhere on the baskets due to hydrophobic-hydrophobic interactions. This can affect the uniformity and completeness of coatings on lenses. In addition, when bubbles are formed in a coating solution, they tends to adhere to baskets and/or trays. Under such circumstance, bubbles can prevent a LbL solution from reaching the surfaces of lenses and result in bubble-defect in the lens coating. Therefore, there is a great need for developing methods and systems for efficiently coating a uniform hydrophilic coat to contact lenses.

Furthermore, when an aqueous LbL coating process is employed to modify the hydrophilic nature of a relatively hydrophobic contact lens material, microorganisms may grow in an aqueous coating solution and produce toxins (exotoxins or endotoxins) that may lead to physiological irritation or mammalian cell death. Such bioburden problem may be prevented by using antibiotics. However, widely using of antibiotics would lead to the proliferation of antibiotics-resistant bacteria. Therefore, there is need for a LbL coating process having a minimized bioburden level.

An object of the invention is to provide a method and system for applying a uniform liquid coating to an ophthalmic lens or a mold used to produce the ophthalmic lens.

Another object of the invention is to provide a LbL coating process having a minimized bioburden level.

SUMMARY OF THE INVENTION

In one aspect of the invention, a method of efficiently applying a coating to each of a plurality of objects comprises dipping the plurality of objects into a bath containing a coating solution containing a coating material and stirring the coating solution with a stirring means or agitating the plurality of the objects in the bath with an agitating means, thereby minimizing the formation of concentration gradients of the coating material in the coating solution around each of the plurality of objects.

In another aspect of the invention, a system for efficiently applying a coating to each of a plurality of objects comprises one or more trays each comprising a plurality of baskets, each of which is capable of holding one of the plurality of objects and a coating solution bath containing a stirring means for stirring the coating solution or containing an agitating means for agitating the trays or containing combination of both, wherein the stirring means or the agitating means or the combination of both are capable of minimizing the formation of concentration gradients of a coating material in the coating solution around each of the plurality of objects.

In still another aspect of the invention, a method for efficiently applying a coating to each of a plurality of objects comprises pre-conditioning a plurality of baskets, loading each of the plurality of objects into one of the plurality of the pre-conditioned baskets, and dipping the plurality of objects into a bath containing a coating solution having a coating material.

In a further aspect of the invention, a LbL coating process, in which the level of bioburden is minimized, comprises dipping a plurality of objects into a coating solution having a pH value of about 2 to 6.5, wherein the coating solution is contained in a disposable plastic liner which is placed in a container and wherein the liner is discarded after use for up to 24 hours.

DETAILED DESCRIPTION OF THE PREFERRED EMBODIMENTS

In one aspect, the present invention provides a method for efficiently applying a coating to each of a plurality of objects comprises dipping the plurality of objects into a bath containing a coating solution having a coating material and stirring the coating solution with a stirring means or agitating the plurality of objects in the bath with an agitating means, thereby minimizing the formation of concentration gradients of the coating material in the coating solution around each of the plurality of objects. The temperature of the coating solution is preferably 14° C.–30° C., more, preferably 16° C.–25° C. A person skilled in the art will know how to control the temperature of a coating solution using a temperture controller.

In a preferred embodiment, the method for efficiently applying a coating to each of a plurality of objects comprises an additional step of removing the plurality of objects from the bath by a removing means or manually. In a further preferred embodiment, the method for efficiently applying a coating to each of a plurality of objects further comprises a step of loading manually or with a loading means each of the plurality of objects into one of baskets before the dipping step and/or a step of unloading manually or with the loading means each of the plurality of objects out of the baskets.

"An object" refers to an ophthalmic lens, a mold for making an ophthalmic lens, or a medical device other than ophthalmic lens.

"A medical device" as used herein refers to a device having surfaces that contact tissue, blood, or other bodily fluids of patients in the course of their operation. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; and (4) ophthalmic lenses.

"An ophthalmic lens", as used herein, refers to a contact lens (hard or soft), or an intraocular lens.

"A coating material" refers to a polymer material that can change the hydrophilic properties of the surface of an object. Exemplary coating materials are polyelectrolytes.

Any known, suitable stirring means can be used in the invention. Preferably, the stirring means is capable of creating a convective current flow and thereby forcing a coating solution flowing over and under each of a plurality of objects to be coated. In this preferred embodiment, the coating solution is constantly mixed and each of the plurality of objects are completely enveloped by a well-mixed coating solution. Therefore, the coating process can be highly efficient.

An exemplary stirring means for creating a convective current flow in the coating bath is an open or closed pumping system that may be attached to a plenum. The plenum is capable of allowing the coating solution to be evenly distributed over each of the plurality of objects.

Any known, suitable agitating means can be used in the invention. Preferably, the agitating means is capable of moving a tray containing a plurality of objects in a linear fashion in the coating bath. In this preferred embodiment, a coating solution in the coating bath is stagnant while the plurality of objects are mechanically moved through the coating solution, thus forcing the coating solution to flow over and under each of the plurality of objects. The coating process according to this embodiment can be highly efficient because the coating solution can completely envelop each of the plurality of objects while it is mixed.

"A tray" refers to a flat device that comprises or carries a plurality of baskets. Trays can be made from any materials that are compatible with a coating solution.

"A basket" refers to an object holding device having a first and a second halves, each of which has openings which allows a fluid to pass through the basket while the object is in place. Generally, baskets are made of a plastic but it can be made of any easily fabricated material. The shape of a basket can be designed to accommodate the shape of an object to be held. Preferably, a basket has a lattice network structure and has a percentage of opening surface over total surface being at least 25%.

Any known, suitable removing means can be used to remove the plurality of objects. An exemplary removing means is a robotic arm which is capable of picking up trays containing the plurality of objects under control of a computer system.

A person skilled in the art can select a known, suitable loading means for loading each of the plurality of objects into one of baskets in a tray or unloading the object out of the baskets. An example of loading means is an air-assisted device that is capable of picking and holding an ophthalmic lens under a negative pressure and of releasing the lens under an even or positive pressure. Loading and/or unloading of ophthalmic lenses can be carried out one lens at one time or preferably more than two lens at one time. Preferably, the loading and/or unloading processes can be carried out automatically under control of a computer system.

In another aspect, the present invention provides a system for efficiently applying a coating to each of a plurality of objects comprises a tray comprising a plurality of baskets, each of which is capable of holding one of the plurality of objects and a coating solution bath containing a stirring means for stirring the coating solution or containing an agitating means for agitating the tray or containing combination of both, wherein the stirring means or the agitating means or the combination of both are capable of minimizing the formation of concentration gradients of a coating material in the coating solution around each of the plurality of objects. In alternative preferred embodiments, the stirring means is capable of creating a convective current flow and thereby forcing a coating solution flowing over and under each of a plurality of objects to be coated, and/or the agitating means is capable of moving a tray containing a plurality of objects in a linear fashion in the coating bath. In a further preferred embodiment, the system of the invention further comprises a removing means for removing the object from the coating bath and/or a loading means for loading each of the objects into one of baskets in a tray or for unloading the objects from the baskets.

An exemplary preferred stirring means is an open or closed pumping system that may be attached to a plenum which capable of allowing the coating solution to be evenly distributed over each of the plurality of objects.

In still another aspect, the present invention provides a method for efficiently applying a coating to each of a plurality of objects comprises pre-conditioning a plurality of baskets which are contained in one or more trays, loading each of the plurality of objects into one of the plurality of the pre-conditioned baskets, and dipping the plurality of objects into a bath containing a coating solution having a coating material. The temperature of the coating solution is preferably about 14° C.–30° C., more preferably about 16° C.–25° C.

"Pre-conditioning a plurality of baskets" refers to one or more processes that improve permanently or temporarily the hydrophilic properties of the surfaces of the plurality of baskets and forms an aqueous layer covering the surfaces of the plurality of baskets.

The hydrophilic properties of the surfaces of the plurality of baskets can be improved permanently by forming a layer of hydrophilic polymer materials. The formation of such layer on baskets can be achieved by using one or more technologies selected from the group consisting of a plasma treatment process, a Langmuir-Blodgett deposition process, a controlled spin casting process, a chemisorption process, a vapor deposition and a layer-by-layer polymer adsorption (LbL coating) process. For example, baskets can be coated with a layer of hydrophilic polymer materials (e.g., polyelectrolytes) by using a LbL coating process with a conditioning solution or first by plasma treatment and subsequent by LbL coating with a conditioning solution. The layer of hydrophilic polymer materials on the surfaces of the baskets can facilitate retaining of an aqueous layer, which can serve as a blanket separating objects from the hydrophobic surfaces of the baskets. The aqueous layer can still allow polyelectrolytes in a LbL coating solution to reach the surfaces of objects in soft contact via the aqueous layer with baskets, because of diffusion of polyelectrolytes in the coating solution.

The hydrophilic polymer material in the conditioning solution can be a coating material which is used in the coating of objects, or can be any polymer material other than the coating material used in coating objects.

Alternatively, the pre-conditioning of baskets can be carried out as follows. Objects may be placed into one of the two halves of the baskets while a tray containing those halves are being conditioned in a conditioning solution. This allows the objects and the tray to be either simultaneously or sequentially conditioned so that both have a non-interactive, hydrophilic surface and an aqueous layer is formed between the surfaces of objects and of the baskets.

Advantages of pre-conditioning of baskets and/or trays are (1) minimizing the interactions between the uncoated surfaces of objects and the surfaces of baskets and (2) preventing bubble formation or bubble adhesion to the baskets and/or tray.

Trays which comprises preconditioned baskets which hold a plurality objects then can be queued in the same conditioning solution awaiting further processing. Such queue may provide production versatility without degradation to the objects or the surfaces of the objects since the potential for the objects to stick to baskets is minimized.

In a further preferred embodiment, full-loaded trays, as they are being processed in a LbL production environment, are place in a way that all objects are mounted vertically. This allows the objects to drain quickly and efficiently and thereby to minimize solution carry-over into the next LbL coating solution.

In a more preferred embodiment, the coating solution is stirred with a stirring means and/or the trays containing the plurality of objects are agitated in the bath with an agitating means, thereby minimizing the formation of concentration gradients of the coating material in the coating solution around each of the plurality of objects and allowing the coating solution to pass over all surfaces of the objects equally. The stirring means is capable of creating a convective current flow and thereby forcing a coating solution flowing over and under each of a plurality of objects to be coated. Preferably, the stirring means is an open or closed pumping system that may be attached to a plenum which capable of allowing the coating solution to be evenly distributed over each of the plurality of objects. The agitating means is capable of moving a tray containing a plurality of objects in a linear fashion in the coating bath.

The methods and systems of the invention can be used to apply a coating to a mold used in forming ophthalmic lenses and thereafter forming an ophthalmic lens within the mold such the ophthalmic lens becomes coated with materials contained in a coating solution.

In general, a mold can be formed by any method known in the art, such as by injection molding. Typically, two mold halves are formed and later joined together such that a cavity can form therebetween. Although it is typically desired that the mold be made from a material having at least some affinity to polyionic materials, virtually all materials known in the art for making molds can be used. For example, various types of thermoplastic material, such as UV-transmissive or UV-opaque thermoplastic materials, can be utilized to form a mold of the present invention. In one embodiment, one portion of the mold is formed from a UV transmissive material, such as polymethylacrylate, so that UV light can later pass through the section to cure a polymerizable material dispensed within the mold. In another embodiment, another portion of the mold is formed from a UV-opaque material that blocks UV light.

Once a mold is formed, various coating materials and/or additives can be applied thereon.

The methods and apparatus of the invention also can be used to apply a coating to a medical device to modify its surface properties and functions.

In a further aspect, the present invention provides a LbL coating process, in which the level of bioburden is minimized, the process comprising dipping a plurality of objects into a coating solution having a pH value of about 2 to 6.5, preferably about 2.5 to 4.5, wherein the coating solution is contained in a disposable plastic liner which is placed in a container and wherein the liner is discarded after use for up to 24 hours.

By using a disposable plastic liner, any biofilm that may have formed on the liner can be removed together with the discarding of the liner.

It has been discovered that when a coating solution has a pH lower than 3, no significant build-up of bioburden level in the coating solution can be observed for a period of time up to one week. It has also been discovered that a coating solution has a pH of about 2.5 to 4.5, no significant build-up of bioburden level in the coating solution can be observed for a period of time up to three days.

Advantage of the LbL coating process of the invention is to cut the production cost of a LbL coating process. There is no need for preparing frequently coating solutions and for incorporating antibiotics in coating solutions.

What is claimed is:

1. A system for efficiently applying a coating to each of a plurality of objects, the system comprising:
1) One or more trays each comprising a plurality of baskets, each of which is capable of holding one of the plurality of objects, wherein the baskets are pre-conditioned to have a first layer of polyelectrolytes and a second layer of aqueous solution or have a mixed layer of polyelectrolytes and aqueous solution on the surfaces of baskets; and
2) a coating solution bath containing a stirring means for stirring the coating solution or containing an agitating means for agitating the trays or containing combination of both, wherein the stirring means or the agitating means or the combination of both are capable of minimizing the formation of concentration gradients of a coating material in the coating solution around each of the plurality of the objects while held in the trays positioned in the coating bath.

2. A system of claim 1, wherein the objects are ophthalmic lenses or molds for making ophthalmic lenses.

3. A system of claim 1, wherein the objects are medical devices other than ophthalmic lenses.

4. A system of claim 1, wherein the stirring means is capable of creating a convective current flow and thereby forcing the coating solution flowing over and under each of the plurality of objects.

5. A system of claim 4, wherein the stirring means is an open or closed pumping system attached to a plenum capable of allowing the coating solution to be evenly distributed over each of the plurality of objects.

6. A system of claim 5, wherein the agitating means is capable of moving the trays containing the plurality of objects in a linear fashion in the coating bath.

7. A system of claim 6, wherein the system further comprises a temperature controller controlling the temperature of the coating solution.

8. A system of claim 7, wherein the system further comprises a removing means for removing the plurality of baskets and/or a loading means for loading each of the plurality of objects into one of the plurality of baskets or for unloading the plurality of objects out of the plurality of baskets.

9. A system of claim 4, wherein the agitating means is capable of moving the trays containing the plurality of objects in a linear fashion in the coating bath.

10. A system of claim 9, wherein the system further comprises a temperature controller controlling the temperature of the coating solution.

11. A system of claim 10, wherein the system further comprises a removing means for removing the plurality of baskets and/or a loading means for loading each of the plurality of objects into one of the plurality of baskets or for unloading the plurality of objects out of the plurality of baskets.

12. A system of claim 1, wherein the agitating means is capable of moving the trays containing the plurality of objects in a linear fashion in the coating bath.

13. A system of claim 1, wherein the system further comprises a temperature controller controlling the temperature of the coating solution.

14. A system of claim 13, wherein the system further comprises a removing means for removing the plurality of baskets and/or a loading means for loading each of the plurality of objects into one of the plurality of baskets or for unloading the plurality of objects out of the plurality of baskets.

* * * * *